US012121400B2

(12) United States Patent
Zahiri et al.

(10) Patent No.: US 12,121,400 B2
(45) Date of Patent: Oct. 22, 2024

(54) ULTRASOUND IMAGING APPARATUS WITH AN ADD-ON VIBRATION INDUCING DEVICE FOR ULTRASOUND ELASTOGRAPHY

(71) Applicant: Clarius Mobile Health Corp., Burnaby (CA)

(72) Inventors: Reza Zahiri, Burnaby (CA); Daniel Rahardja, Burnaby (CA); Binda Zhang, Surrey (CA); Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 0 days.

(21) Appl. No.: 16/845,055

(22) Filed: Apr. 9, 2020

(65) Prior Publication Data
US 2020/0323517 A1     Oct. 15, 2020

Related U.S. Application Data

(60) Provisional application No. 62/831,925, filed on Apr. 10, 2019.

(51) Int. Cl.
*A61B 8/08*     (2006.01)
*A61B 8/00*     (2006.01)

(52) U.S. Cl.
CPC ............... *A61B 8/485* (2013.01); *A61B 8/56* (2013.01)

(58) Field of Classification Search
CPC ......... A61B 8/485; A61B 8/56; A61B 8/4411; A61B 8/4416; A61B 8/463; A61B 8/465;
(Continued)

(56) References Cited

U.S. PATENT DOCUMENTS

| 6,770,033 B1 | 8/2004 | Fink et al. |
| 7,578,789 B2 | 8/2009 | Sandrin et al. |

(Continued)

FOREIGN PATENT DOCUMENTS

| CN | 104644209 A | * 5/2015 | ............... A61B 8/44 |
| WO | 2017062553 | 4/2017 | |

(Continued)

OTHER PUBLICATIONS

Mellema DC, Song P, Kinnick RR, Urban MW, Greenleaf JF, Manduca A, Chen S. Probe Oscillation Shear Elastography (PROSE): A High Frame-Rate Method for Two-Dimensional Ultrasound Shear Wave Elastography. IEEE Trans Med Imaging. Sep. 2016;35(9):2098-106 (Year: 2016).*

(Continued)

*Primary Examiner* — Baisakhi Roy
*Assistant Examiner* — Kaitlyn E Sebastian
(74) *Attorney, Agent, or Firm* — Julian Ho; Susan Ben-Oliel

(57) ABSTRACT

An ultrasound imaging system including an ultrasound imaging apparatus operable to acquire ultrasound image data and an add-on vibration inducing device operable to generate shear waves. The add-on vibration inducing device is connected cordlessly to the ultrasound imaging apparatus. The add-on vibration inducing device can be powered and controlled by the ultrasound imaging apparatus. The add-on vibration inducing device includes a connector to scanner which connects cordlessly to a power connector on the ultrasound imaging apparatus for transmitting the power and the control signals from the ultrasound imaging apparatus to the add-on vibration inducing device. The ultrasound imaging apparatus can be used separately from the add-on vibration inducing device for ultrasound imaging procedures and the add-on vibration inducing device can be easily (Continued)

mounted on the ultrasound imaging apparatus when the user wishes to perform an elastography diagnostic procedure.

20 Claims, 7 Drawing Sheets

(58) Field of Classification Search
CPC .......... A61B 8/5246; A61B 8/44; A61B 8/54; A61B 8/4427; A61B 8/4455; A61B 8/4477; A61B 8/4433; A61B 8/4209; A61B 8/4472; H04M 1/21
See application file for complete search history.

(56) References Cited

U.S. PATENT DOCUMENTS

| | | | |
|---|---|---|---|
| 8,267,865 B2 | 9/2012 | Hoyt et al. | |
| 8,394,026 B2 | 3/2013 | Eskandari et al. | |
| 8,668,647 B2 | 3/2014 | Eskandari et al. | |
| 8,988,911 B2* | 3/2015 | Norris .................. | H04R 3/00 363/126 |
| 9,801,615 B2 | 10/2017 | Salcudean et al. | |
| 2002/0107538 A1* | 8/2002 | Shibata .......... | A61B 17/320068 606/169 |
| 2004/0249318 A1* | 12/2004 | Tanaka .......... | A61B 17/320068 601/2 |
| 2010/0222723 A1* | 9/2010 | Hoffmann ............... | A61N 7/00 601/107 |
| 2010/0262005 A1* | 10/2010 | Karasawa ............ | A61B 8/5207 600/443 |
| 2012/0123263 A1* | 5/2012 | Osaka .................. | A61B 5/0051 600/438 |
| 2015/0366538 A1* | 12/2015 | McKenna ............. | H02J 7/0044 600/437 |
| 2016/0235621 A1* | 8/2016 | Choe .................. | A61H 23/0236 |
| 2017/0014098 A1 | 1/2017 | Shao et al. | |
| 2017/0333005 A1 | 11/2017 | Chen et al. | |
| 2018/0014811 A1* | 1/2018 | Sonnenschein ...... | A61B 8/4472 |
| 2018/0161004 A1* | 6/2018 | Son ...................... | A61B 8/4455 |
| 2018/0280001 A1* | 10/2018 | Iwama ................. | A61B 8/4427 |
| 2018/0296191 A1 | 10/2018 | Mellema et al. | |
| 2018/0344294 A1 | 12/2018 | Chan et al. | |
| 2019/0231318 A1* | 8/2019 | Audiere ................ | A61B 8/429 |
| 2020/0022678 A1* | 1/2020 | McLaughlin ......... | A61B 8/4254 |
| 2020/0029934 A1* | 1/2020 | Sandrin ................ | A61B 8/4494 |
| 2020/0054217 A1* | 2/2020 | Parker ................. | A61B 5/7239 |
| 2021/0018606 A1* | 1/2021 | McCaw ................ | G01N 29/34 |

FOREIGN PATENT DOCUMENTS

| | | |
|---|---|---|
| WO | 2018078002 | 5/2018 |
| WO | 2018177991 | 10/2018 |

OTHER PUBLICATIONS

Mellema (NPL "Probe Oscillation Shear Elastography (PROSE)" 2016) (Year: 2016).*

Li, Guo-Yang, et al. (2017). "Mechanics of ultrasound elastography", in Proceedings of The Royal Society A 473:20160841, https://doi.org/10.1098/rspa.2016.0841, last accessed Jun. 9, 2020.

* cited by examiner

ULTRASOUND IMAGING APPARATUS WITH AN ADD-ON VIBRATION INDUCING DEVICE FOR ULTRASOUND ELASTOGRAPHY

CROSS-REFERENCE TO RELATED APPLICATION

This application claims the benefit of U.S. Provisional Patent Application No. 62/831,925 entitled "ULTRASOUND IMAGING APPARATUS WITH AN ADD-ON VIBRATION INDUCING DEVICE FOR ULTRASOUND ELASTOGRAPHY" filed on Apr. 10, 2019, is incorporated by reference it its entirety in this disclosure.

TECHNICAL FIELD

The present disclosure relates to an ultrasound imaging apparatus, and, in particular, to an ultrasound imaging apparatus with an add-on vibration inducing device for ultrasound elastography.

BACKGROUND OF THE INVENTION

Ultrasound shear wave elastography is an ultrasound technique that can assess, in a non-invasive way, the mechanical properties of a patient's tissue, for example elasticity and stiffness which are indicative of the health state of the tissue and therefore have great application in the medical field, for example for liver fibrosis staging and cancer diagnosis.

Through elastography, shear waves are introduced in the tissue being examined and shear propagation parameters such as propagation speed, attenuation, shear modulus, shear viscosity, storage modulus, loss modulus, Young's modulus, and mechanical relaxation time can be detected.

The shear waves can be generated by an external mechanical vibrator and can be continuous (as used in the continuous elastography method) or transient (as used in the transient elastography method). In continuous vibration methods the shear waves are present in the tissue at all times and this helps capturing changes in the muscle stiffness.

Some systems used in elastography employ a handheld vibrator generating the mechanical vibration, positioned adjacent to an ultrasound transducer which measures the shear waves generated by the vibrator. Such systems require the operator to use both hands, one to hold the vibrator and one to hold the transducer. This requirement limits the clinical value of the system since it forces the operator to operate the vibrator and the ultrasound transducer at the same time while scanning the tissue being examined.

In order to improve such systems and have the operator use only one hand during an elastography scanning process, some existing devices include an ultrasound probe including a probe casing, at least one ultrasound transducer having a symmetry axis, and a vibrator placed within the probe casing and arranged to induce the movement of the probe casing along the symmetry axis of the ultrasound transducer, as described for example in PCT publication number WO2018177991. The ultrasound transducer is bound to the probe casing with no motion of the ultrasound transducer relative to the probe casing.

Similarly, PCT publication number WO2018078002 describes a probe for transient elastography including a probe casing, at least one ultrasound transducer and a vibrator being located inside the probe casing with no motion of the ultrasound transducer with respect to the probe casing.

While such solutions improve the maneuverability of such probes for use in ultrasonic elastography, such ultrasound probes where the vibrator system is placed within the probe casing are difficult to use for other ultrasound procedures beside elastography.

Some existing prior art documents propose to have an actuator coupled to an ultrasound transducer, for example attached directly to the outer surface of the transducer as illustrated, for example, in FIG. 1 of United States patent publication number 20170333005 to allow a single-handed operation of the probe by eliminating the need for a separate vibration source. The actuator provides the continuous vibration to the transducer, and at least one shear wave is induced by the continuous vibration of the transducer. As mentioned in this patent application, it may be preferred to align the actuator co-axially with the transducer so that the transducer motion is primarily axial with minimal transverse and azimuthal motions. This prior art document does not further describe how such an arrangement would be achieved, how the actuator is coupled to the transducer and how the actuator is powered. It also shows that the actuator is permanently attached to the transducer.

Another prior art document, U.S. Pat. No. 6,770,033 illustrates an imaging device using shear waves which employs an acoustic transducer for generating acoustic waves such as vibrator controlled by a microcomputer and a separate ultrasound probe or, in a variant illustrated in FIG. 2, it describes an ultrasound probe carried by the vibrator which involves the motion of the probe generating the shear wave. No further description is given on how the ultrasound probe is attached to the vibrator, how they are powered or how they connect to each other.

In the documents presented in the prior art, the ultrasound transducer generally appears permanently coupled to the vibration generating device to form an apparatus that is dedicated to elastography diagnostic methods.

In view of the known difficulties associated with an elastography method for accurately diagnosing the health of a patient's tissue and any possible diseases, there is still a need for an imaging system capable of inducing mechanical vibrations and scanning a patient's tissue using an ultrasound transducer which does not require the user to exercise both hands during operation and allows at the same the independent use of the ultrasound probe without the vibration device for other diagnostic methods, while allowing an easy and convenient coupling of the ultrasound probe and of the vibrator for ultrasound elastography diagnostic methods.

The embodiments discussed herein addresses the need identified above. The foregoing examples of the related art and limitations related thereto are intended to be illustrative and not exclusive. Other limitation of the related art will become apparent to those of skill in the art upon a reading of the specification and a study of the drawings herein.

BRIEF DESCRIPTION OF THE DRAWINGS

Non-limiting examples of the present disclosure will be described in relation to the drawings, in which.

DETAILED DESCRIPTION

Figure 1:
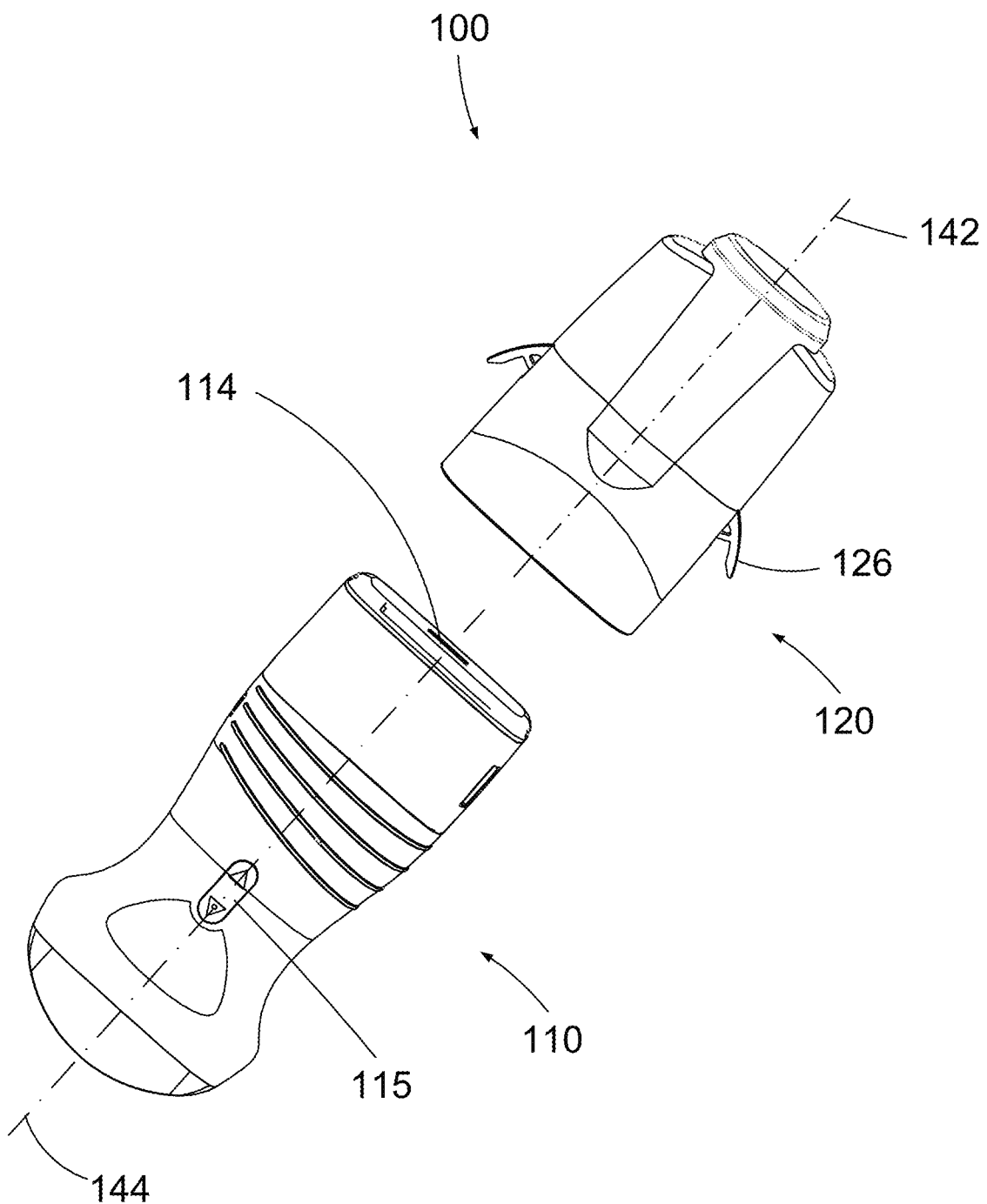
FIG. 1 shows a perspective view of an ultrasound imaging system with an add-on vibration inducing device in a detached state from the ultrasound imaging apparatus, in accordance with at least one embodiment of the present invention.

In a first broad aspect of the present disclosure, there is provided an ultrasound imaging system including: an ultrasound imaging apparatus operable to acquire ultrasound image data; and an add-on vibration inducing device operable to generate shear waves, wherein the add-on vibration inducing device is connected cordlessly to the ultrasound imaging apparatus for performing elastography diagnostic methods.

In some embodiments, the cordless connection between the add-on vibration inducing device and the ultrasound imaging apparatus is done through a connector to scanner on the add-on vibration device which connects cordlessly to a power connector on the ultrasound imaging apparatus for transmitting the power and/or the control signals from the ultrasound imaging apparatus to the add-on vibration inducing device.

In some embodiments, the ultrasound imaging apparatus has a battery which powers the add-on vibration inducing device through the connection between the power connector and the connector to scanner.

In some embodiments, the longitudinal axis of the add-on vibration inducing device coincides with the longitudinal axis of the ultrasound imaging apparatus. In other embodiments, the longitudinal axis of the add-on vibration inducing device can be parallel with the longitudinal axis of the ultrasound imaging apparatus.

In some embodiments, the add-on vibration inducing device is mounted on the ultrasound imaging apparatus through a lock feature provided on the ultrasound imaging apparatus which cooperates with a lock feature provided on the add-on vibration inducing device such that the add-on vibration inducing device is held in a fixed position relative to the ultrasound imaging apparatus, and the shear waves signals generated by the add-on vibration inducing device are securely transmitted to the ultrasound imaging apparatus.

In some embodiments, the lock feature on the add-on vibration inducing device includes a rod which can be positioned to fit within the lock feature provided on the ultrasound imaging apparatus which is in the shape of a channel.

In some embodiments, the add-on vibration inducing device includes a voice coil actuator which moves coaxially to generate shear waves signals which are transmitted to the ultrasound imaging apparatus.

In some embodiments, a bearing block is attached either directly or through an intermediary component to a housing of the vibration inducing device and a linear rail is attached to a housing of the voice coil actuator such that the bearing block and the linear rail cooperate to allow the co-axial motion of the voice coil actuator.

In some embodiments, the add-on vibration inducing device further includes a first stage DC/DC converter for limiting the voltage transmitted from the battery of the ultrasound imaging apparatus to the vibration inducing device when the ultrasound imaging apparatus needs more power, a first capacitor which transmits the power from the first stage DC/DC converter to a second stage DC/DC converter which regulates the voltage transmitted through a second capacitor to a voice coil actuator driver which controls and monitors the voice coil actuator.

In some embodiments, the add-on vibration inducing device includes a microcontroller which controls the voice coil actuator driver to thereby control the vibration signals generated by the add-on vibration inducing device according to the commands transmitted by the ultrasound imaging apparatus.

In some embodiments, the ultrasound imaging apparatus is wired to a user interface device or it is wirelessly connected to a user interface device which transmits control signals to the ultrasound imaging apparatus and to the add-on vibration inducing device.

In other embodiments, the add-on vibration inducing device is activated by a push button located on the ultrasound imaging apparatus or is activated by a user interface device communicably coupled to the ultrasound imaging apparatus.

In some embodiments, the cordless connection between the ultrasound imaging apparatus and the add-on vibration inducing device is through a wireless, radio-wave based, communication interface such as a Bluetooth interface.

In the present invention, the ultrasound imaging apparatus is configured to be used separately of the add-on vibration inducing device for ultrasound imaging diagnostics other than elastography methods. For this purpose, the add-on vibration inducing device can be detached from the ultrasound imaging apparatus.

In another broad aspect of the present disclosure, there is provided a method for operating an ultrasound imaging system which includes an ultrasound imaging apparatus cordlessly connected to an add-on vibration inducing device to generate shear waves for performing an elastography diagnostic procedure, the method including: generating an activation signal through a push button on the ultrasound imaging apparatus or through a user interface device connected to the ultrasound imaging apparatus, and transmitting the activation signal from the ultrasound imaging apparatus through a cordless connection to the add-on vibration inducing device to command it to generate shear waves for performing an elastography diagnostic method.

In some embodiments, the cordless connection from the ultrasound imaging apparatus to the add-on vibration inducing device is done through a power connector located on the ultrasound imaging apparatus which communicates with a connector to scanner located on the add-on vibration inducing device.

In some embodiments, the method further includes providing electrical power from a battery located within the ultrasound imaging apparatus to the add-on vibration inducing device through the power connector which communicates with the connector to scanner.

In some embodiments, the method further includes limiting the electrical power transmitted from the battery through a first DC/DC converter to a first capacitor of the add-on vibration device when the ultrasound imaging apparatus needs more power and providing stable regulated power to a driver of a voice coil actuator from the first capacitor through a second stage DC/DC converter and through a second capacitor to a driver of a voice coil actuator when the activation signal for generating shear wave signals is received from the ultrasound imaging apparatus.

In some embodiments, the method further includes controlling and monitoring the operation of the driver of the voice coil actuator by a microcontroller according to commands received by the microcontroller from the ultrasound imaging apparatus and providing feedback from the voice coil actuator to the microcontroller.

In some embodiments, the cordless connection from the ultrasound imaging apparatus to the add-on vibration inducing device is done through a wireless, radio-wave based, communication interface such as a Bluetooth interface.

In another broad aspect of the present disclosure, there is provided a user interface device substantially as described herein.

In another broad aspect of the present disclosure, there is provided an ultrasound imaging apparatus substantially as described herein.

In another broad aspect of the present disclosure, there is provided an add-on vibration inducing device substantially as described herein.

In another broad aspect of the present disclosure, there is provided an ultrasound imaging system substantially as described herein.

In another broad aspect of the present disclosure, there is provided a method substantially as described herein.

In another broad aspect of the present disclosure, there is provided a computer readable medium storing instructions for execution by one or more processors for performing a method substantially as described herein or providing a user interface substantially as described herein.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is an ultrasound imaging system in accordance with an embodiment of the present invention. The ultrasound imaging system 100 includes an ultrasound imaging apparatus 110 (also generally called a "scanner" herein) and an add-on vibration inducing device 120 shown in a detached state. As illustrated, the ultrasound imaging apparatus is provided in the form of a handheld wireless scanner that may be configured to communicate with an external wireless computing device (e.g. a tablet computer) containing a display (not shown). In various embodiments, the ultrasound imaging apparatus 110 may be provided in the form of an ultrasound probe that can be attached via a cord to a smart device (e.g. smartphone or tablet computer) or to a separate ultrasound machine.

The ultrasound imaging apparatus 110 contains a transducer and can operate as a standalone, separate device with the transducer configured to transmit ultrasound energy signals toward an object and receive echoes of the ultrasound energy signals that reflect off the object. In the illustrated embodiment the ultrasound imaging apparatus 110 communicates wirelessly with an external computing device, and contains a battery for providing power to the electronics within the ultrasound imaging apparatus 110 which are required for emitting the ultrasound energy signals.

The ultrasound imaging apparatus 110 is configured to be connected to the add-on vibration inducing device 120 when it is desired to perform a diagnostic using an ultrasound shear wave elastography method. For this purpose, the ultrasound imaging apparatus 110 includes a lock feature in the shape of a channel as further described and illustrated in FIG. 3, and a power connector 114 which are matched with corresponding features on the add-on vibration inducing device 120 when the add-on vibration inducing device 120 is attached to the ultrasound imaging apparatus 110. The corresponding features on the add-on vibration inducing device 120 consist of a lock 126 and a connector to scanner 124, for example, as illustrated in FIG. 4.

Figure 2:
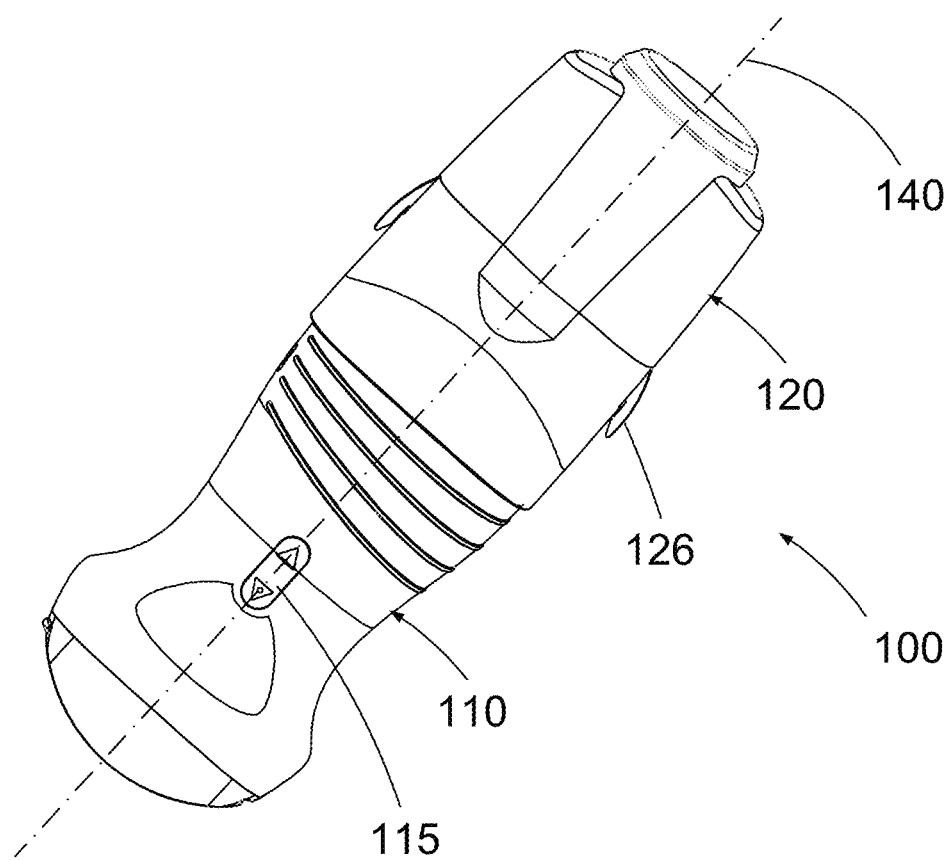
FIG. 2 shows a perspective view of the ultrasound imaging system illustrated in FIG. 1 with the add-on inducing device attached to the ultrasound imaging apparatus, in accordance with at least one embodiment of the present invention.

The assembled ultrasound imaging system 100 including the add-on vibration inducing device 120 mounted on the ultrasound imaging apparatus 110 is illustrated in FIG. 2. In the example embodiment illustrated in FIGS. 1 and 2 the ultrasound imaging apparatus is provided with a push button 115 for activating the vibration inducing device 120 when desired.

Figure 3:
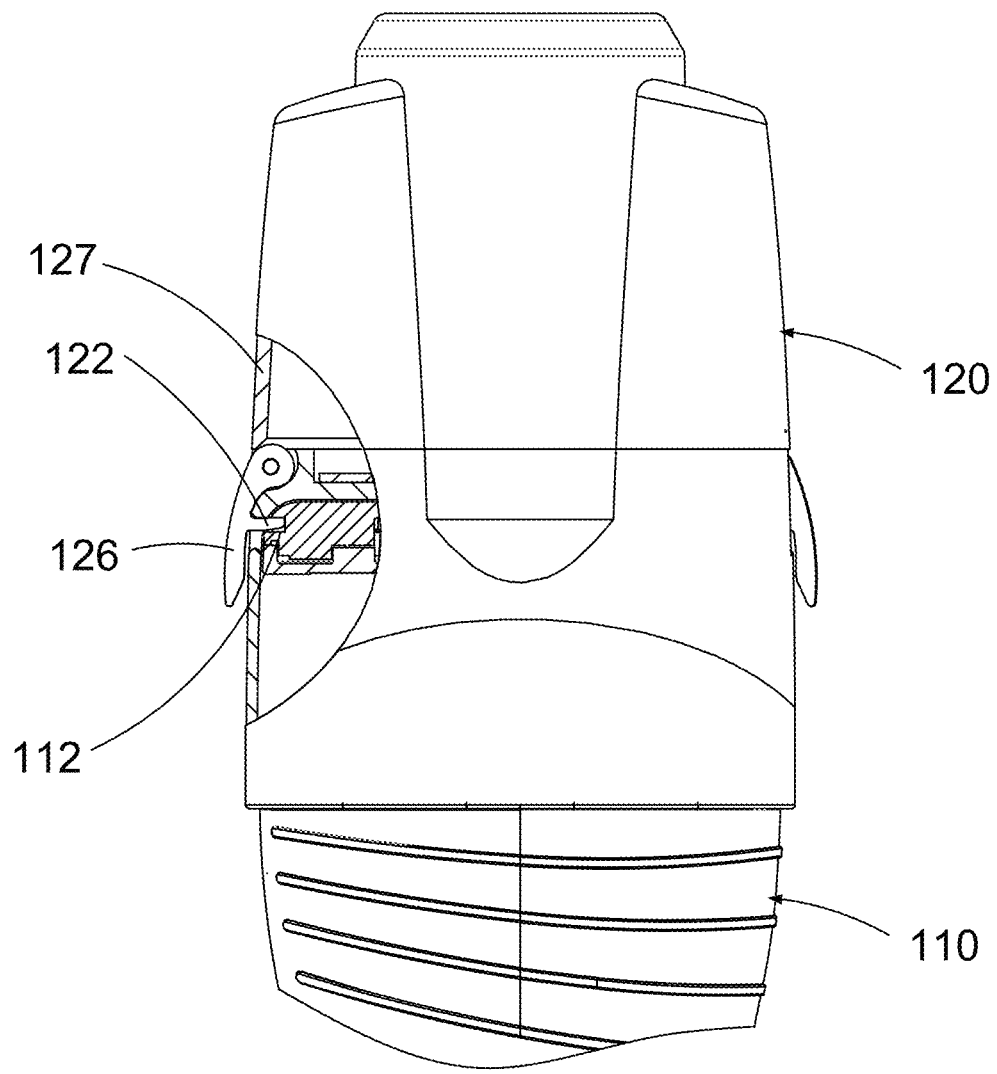
FIG. 3 shows a detail view of the attachment system between the ultrasound imaging apparatus and the add-on vibration inducing device in the ultrasound imaging system illustrated in FIG. 1, in accordance with an embodiment of the present invention.
Figure 4:
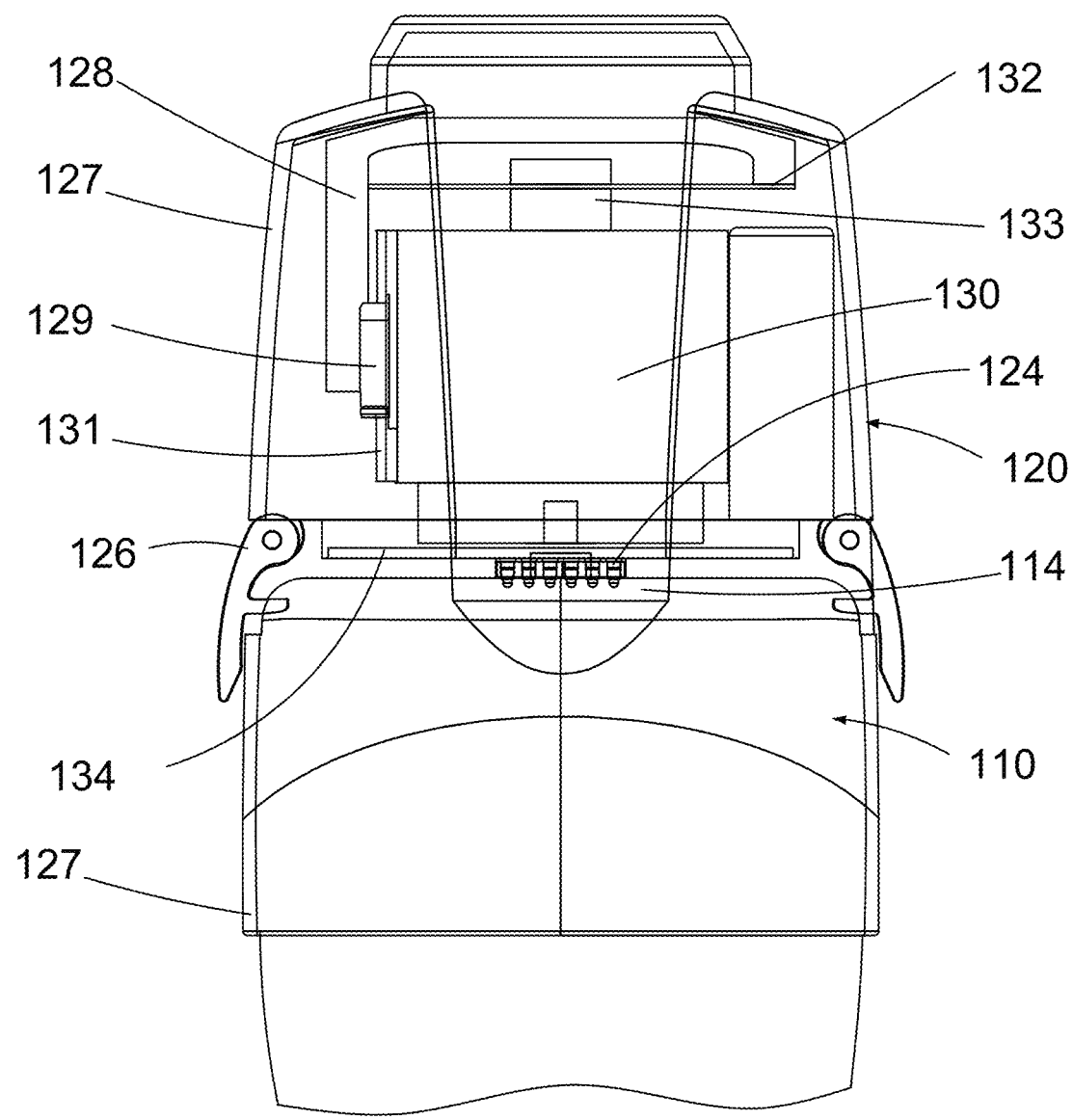
FIG. 4 shows a view of the add-on vibration inducing device attached to the ultrasound imaging apparatus showing the components of the add-on vibration inducing device, in accordance with at least one embodiment of the present invention.

An embodiment of the lock features for connecting the add-on vibration inducing device to the ultrasound imaging apparatus of the present ultrasound imaging system is better illustrated in FIG. 3. In this embodiment, the lock feature of the ultrasound imaging apparatus 110 includes a channel 112 provided in its housing and the add-on vibration inducing device 120 includes a lock 126 which is attached to its housing 127 and which is provided with a rod 122. When the user rotates the lock 126, rod 122 is moved from an unlatched position illustrated for example in FIG. 1 to a latched position illustrated in FIG. 3 in which it is locked within the channel 112 of the ultrasound imaging apparatus.

In various embodiments, other lock features for coupling the add-on vibration inducing device 120 to the ultrasound imaging apparatus 110 can be provided for securing a fixed relative position between these two components of the present ultrasound imaging system.

In preferred embodiments, when the add-on vibration inducing device 120 is mounted on the ultrasound imaging apparatus 110, the vertical axis 142 of the add-on vibration inducing device 120 aligns with the vertical axis 144 forming the longitudinal symmetry axis 140 of the present ultrasound imaging system 100 as illustrated in FIGS. 1 and 2. In other embodiments the vertical axis 142 of the add-on vibration inducing device 120 can be parallel or inclined relative to the vertical axis of the ultrasound imaging apparatus 110 and they do not form a common longitudinal axis.

As illustrated in FIG. 4 in a schematic representation, the add-on vibration inducing device 120 includes a voice coil actuator 130 which, in some embodiments, is powered by the battery of the ultrasound imaging apparatus through the connection between the power connector 114 of the ultrasound imaging apparatus 110 and the connector to scanner 124 of the add-on vibration inducing device 120. When powered, the voice coil actuator 130 generates low-frequency elastic waves which are transmitted through the ultrasound imaging apparatus 110 to the examined tissue when the ultrasound imaging apparatus 110 is held in contact with the skin of the patient being examined. The propagation of this low-frequency elastic waves is analyzed by means of high-frequency ultrasonic waves emitted and received by the ultrasound imaging apparatus 110 during the propagation of the low-frequency elastic waves. The add-on vibration inducing device 120 can be controlled to generate either a single vibration pulse when the system is used for the transient elastography methods or a train of vibration pulses as is done during the continuous elastography methods. The present system therefore enables and can be adapted for different elastography techniques.

The activation of the add-on vibration inducing device 120 for generating vibration waves can be triggered by one or more push buttons 115 placed on the ultrasound imaging apparatus 110, which triggers the activation of the voice coil actuator 130 through the communication transmitted between the power connector 114 and the connector to scanner 124.

In some embodiments, where the ultrasound imaging apparatus 110 is wired to or it is wirelessly connected to a user interface device, the activation of the voice coil actuator can be done instead through a command generated by a computer application on the user interface device which is transmitted through the ultrasound imaging apparatus to the add-on vibration inducing device through the connectors 114 and 124.

Referring to FIG. 4, in some embodiments, the add-on vibration inducing device 120 further includes a bracket 128 which is attached to its housing 127 and which carries a bearing block 129 which is maintained in fixed position relative to the housing 127. The housing of the voice coil actuator 130 carries a linear rail 131 which is configured to cooperate with the bearing block 129 to allow the coaxial motion of the voice coil actuator 130 for generating the vibration pulses used for elastography.

In some embodiments, the bracket 128 of the housing 127 carries a leaf spring 132 and a leaf spring clamp 133 which comes into contact with the housing of the voice coil actuator 130 for keeping it in a home position when the voice coil actuator is not activated.

The add-on vibration inducing device 120 further includes other electronic components besides the voice coil actuator 130 which are carried by a printed circuit board assembly 134. In other embodiments, the electronic components can be contained in several printed circuit board assemblies with cable connections between them.

In various embodiments, the materials of the housing 127 and bracket 128 may be of a sufficient strength and durability to withstand the repeated vibration pulses created by the voice coil actuator 130. For example, the housing may be formed using appropriate plastics. At the same time, it may be ergonomically desirable for the weight of an add-on vibration inducing device 120 to not be exceedingly heavy. Thus, in some embodiments, the weight of the add-on vibration inducing device 120 may be configured to between 100 and 1000 grams. In some further embodiments, the weight of an add-on vibration inducing device may be configured to between 440 and 800 grams.

Figure 5:
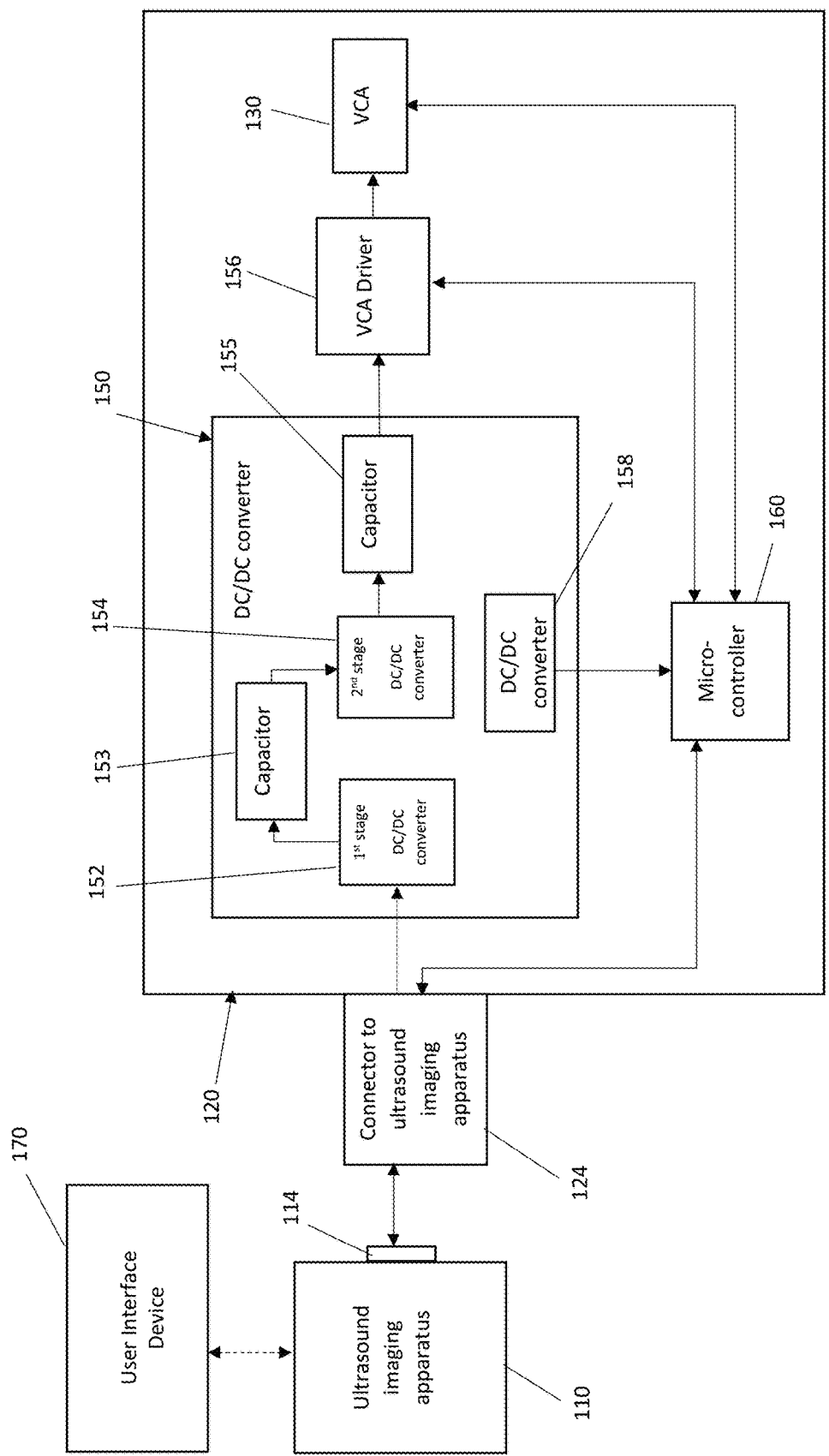
FIG. 5 shows a schematic of the components of the present ultrasound imaging system, and in particular, it shows a schematic of the components of the add-on vibration inducing device and how they connect to each other and to the ultrasound imaging apparatus in accordance with at least one embodiment of the present invention.

The electronic components of the add-on vibration inducing device 120 are schematically illustrated in FIG. 5 which also shows the connection between these electronic components and the ultrasound imaging apparatus 110 and the user interface device 170.

As shown in FIG. 5 the ultrasound imaging apparatus 110 is electrically connected through its power connector 114 and through the connector to scanner 124 to the add-on vibration inducing device 120. The connector to scanner 124 is connected to a DC/DC converter assembly 150 which includes a first stage DC-DC converter 152 which limits the current taken by the add-on vibration inducing device 120 from the ultrasound imaging apparatus 110 for predetermined periods of time to charge the bulk capacitor 153 such that the DC/DC converter 150 does not draw too much current from the battery of the ultrasound imaging apparatus when both the ultrasound imaging apparatus and the add-on vibration inducing device need to operate. The DC/DC converter assembly further includes a second stage DC/DC converter 154 which is powered by the bulk capacitor 153 and which provides a stable regulated voltage through a second bulk capacitor 155 to the voice coil actuator (VCA) driver 156 of the voice coil actuator 130. The bulk capacitors help maintain a stable regulated voltage for the voice coil actuator driver.

In various embodiments, the DC/DC converter assembly 150 may also include a third DC/DC converter 158 which provides power to a microcontroller 160. The microcontroller 160 controls the voice coil actuator driver 156 (frequency, pulse duration, duty cycle, gain, etc.) according to the commands received from the ultrasound imaging apparatus 110 (generated, for example, by activating the one or more push buttons 115 or by a software or other application on the user interface device 170) and monitors the operation of the voice coil actuator driver. As noted, the user interface device 170 can be wired to the ultrasound imaging apparatus 110 or can be wirelessly connected to the ultrasound imaging apparatus 110.

In some embodiments, a debug connector (not illustrated) can be connected to the microcontroller 160 to program it and debug it when necessary.

The present embodiments cover any type of cordless connection between the ultrasound imaging apparatus 110 and the add-on vibration inducing device 120, so long as no cable or cord is used to provide a connection between the two when they are attached (e.g., to perform elastography methods). In the illustrated example embodiment of FIGS. 1-4, the connection between the ultrasound imaging apparatus 110 and the add-on vibration inducing device 120 is provided with electrical connectors 114, 124. However, other ways of establishing this connection cordlessly may be possible.

For example, in some embodiments, the communication between the ultrasound imaging apparatus and the add-on vibration inducing device can be done by a wireless interface (e.g., a radio-wave based communication interface such as Bluetooth™ or Wi-Fi™) instead of using the power connectors 114 and 124. In these embodiments, the add-on vibration inducing device may have its own battery which powers the electronic components within the add-on vibration inducing device 120 described above. In such embodiments the microcontroller still receives the commands from the ultrasound imaging apparatus triggered by a push button or by a user interface device which can be wired to the ultrasound imaging apparatus or wirelessly connected thereto.

The ultrasound imaging system of the present invention operates as described below. The connector to scanner 124 on the add-on vibration inducing device 120 is connected to power connector 114 of the ultrasound imaging apparatus 120 and power is continuously provided by the battery of the ultrasound imaging apparatus 110 to the DC/DC converter assembly 150, more specifically to the first stage DC/DC converter 152 which limits the current taken from the scanner 110 for predetermined periods of time to charge the bulk capacitor 153 so that the DC/DC converter does not draw too much current from the battery of the ultrasound imaging apparatus 110 when both the ultrasound imaging apparatus 110 and the add-on vibration inducing device 120 need to operate.

When an activation signal is sent by the user through the one or more push buttons 115 on the ultrasound imaging apparatus 110 or through an application on the user interface device 170, the bulk capacitor 153 can provide current to the second stage DC/DC converter 154 to generate and transmit, through the bulk capacitor 155, a stable regulated voltage for the voice coil actuator driver 156 which starts to generate shear wave signals.

The microcontroller 160 may control the voice coil actuation driver 156 (frequency, pulse duration, duty cycle, gain, etc.) according to the commands received from the ultrasound imaging apparatus 110 and monitor the operation of the voice coil actuator driver 156.

In various embodiments, the microcontroller 160 may also receive feedback from the voice coil actuator 130 to monitor whether the desired parameters for driving the voice coil actuator (e.g., as sent from the microcontroller 160 to the VCA driver 160) were in fact performed by the VCA 130. For example, there may be scenarios where the characteristics (e.g., frequency, profile) of the vibration pulse(s) generated by the VCA 13 do not match the desired characteristics, and this may affect the resulting measurements. By having the microcontroller 160 also receive feedback from the VCA 130 to monitor characteristics of the actual outputted vibration pulse(s), this information may be communicated back to the ultrasound imaging apparatus 110 so that the ultrasound imaging apparatus 110 can take it into account when performing the elastography measurements. Additionally or alternatively, this feedback can be used to control the voice coil actuator driver 156 to adjust the parameters provided to the VCA driver 156, so as to better obtain the desired vibration pulse(s) characteristics. In various embodiments, the microcontroller 160 may not monitor the output of the VCA 130 directly, but instead, there may be a sensor positioned between the VCA 130 and the microcontroller 160. This sensor may then monitor the output of the VCA 130, and provide such information to the microcontroller 160. Embodiments with this type of feedback circuit that monitors characteristics of the vibration pulse(s) generated by the VCA 130 can be considered a closed-loop solution.

In various embodiments, additionally or alternatively, the feedback information may be obtained from an inertial measurement unit (IMU) provided within the ultrasound imaging apparatus 110. For example, in an example embodiment, the feedback circuit may not be provided on the add-on vibration inducing device 120 at all and the IMU may be used to measure the characteristics of the vibration pulse generated by the VCA 130 (the characteristics of which was transferred to the ultrasound imaging apparatus 110). In another example embodiment, the feedback circuit may be left intact in the add-on vibration inducing device 120, and the information from the IMU can be used to confirm or corroborate the information measured by the microcontroller 160.

The shear waves generated by the voice coil actuator may be transmitted through the ultrasound imaging apparatus 110 to the tissue being examined and shear propagation parameters such as propagation speed, attenuation, shear modulus, shear viscosity, storage modulus, loss modulus, Young's modulus, and mechanical relaxation time can be detected by the ultrasound imaging apparatus 110.

The shear waves generated by the present add-on vibration inducing device 120 can be continuous (as used in the continuous elastography method) or transient (as used in the transient elastography method).

In the embodiments shown herein, the connection between the ultrasound imaging apparatus 110 and the add-on vibration inducing device 120 is provided via an electrical connection between connectors 114, 124 on the respective devices. As noted above, in these embodiments, to initiate a vibration pulse, a push button 115 can be activated on the ultrasound imaging apparatus 110 to communicate an electrical signal to the add-on vibration inducing device 120. Because there is an electrical connection between the imaging apparatus 110 and the add-on vibration inducing device 120, the delay between when the push button 115 is activated to when the vibration pulse is generated is minimal and delivery of the vibration pulse will generally be synchronized with the clock of a processor executing on the ultrasound imaging apparatus 110. However, in various embodiments where the communication between the ultrasound imaging apparatus 110 and the add-on vibration inducing device 120 is provided via a wireless, radio-wave based communication interface (such as a Bluetooth interface), there may potentially be a small lag (e.g., due to latency or interference) compared to when the vibration pulse is generated when the activation signal is delivered using a direct, electrical connection between the ultrasound imaging apparatus 110 and the add-on vibration inducing device 120. In these embodiments, the IMU discussed above may also be used to measure when the vibration pulse actually gets delivered by the add-on vibration inducing device 120. In case there is any lag between when the signal is transmitted to the add-on vibration inducing device 120 and when the vibration pulse(s) actually gets generated, the IMU may be used to sense when the vibration pulse(s) actually gets delivered so as to start elastography measurements at the appropriate time. In this way, the IMU may be used to help synchronize operation between the ultrasound imaging apparatus 110 and the add-on vibration inducing device 120. This synchronization may be performed additionally or alternatively to the feedback circuit operation discussed above that measures the characteristics of the vibration pulse delivered by the add-on vibration inducing device 120.

Figure 6:
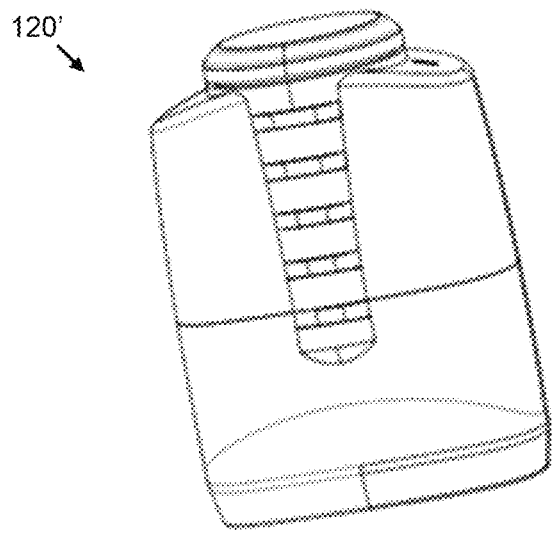
FIG. 6 shows a perspective view of an add-on vibration inducing device, in accordance with at least one other embodiment of the present invention.

Referring to FIG. 6, shown there generally as 120' is a perspective view of an add-on vibration inducing device, in accordance with at least one other embodiment of the present invention. Operation of this add-on vibration inducing device 120' is similar to the add-on vibration inducing device 120 discussed above with respect to FIGS. 1-5, except the lock feature is provided on the interior of the housing to provide a smoother exterior surface on the add-on vibration inducing device 120'. For example, this may allow for ease of cleaning the exterior surface of the add-on vibration inducing device 120'.

Figure 7:
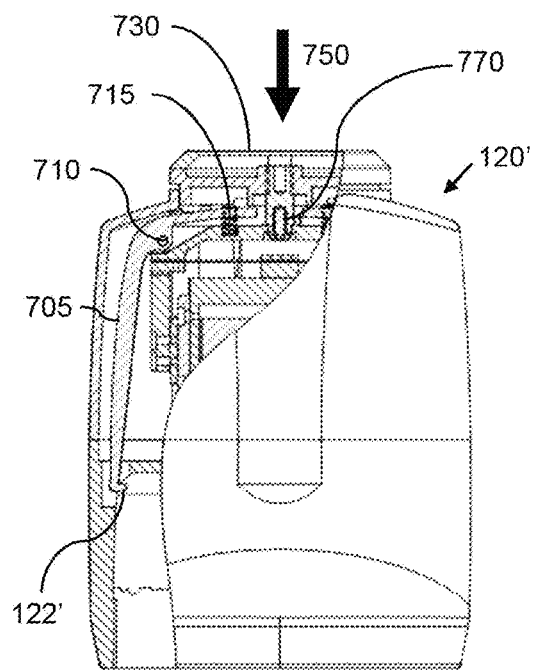
FIGS. 7-8 shows detailed views of the attachment system in the add-on vibration inducing device of FIG. 6, in accordance with at least one embodiment of the present invention.

Referring to FIG. 7, shown there is a detailed view of the attachment system in the add-on vibration inducing device 120' of FIG. 6, in accordance with at least one embodiment of the present invention. On the interior of the add-on vibration inducing device 120', there may be provided a clamp arm 705. The add-on vibration inducing device 120' may be provided with a pair of symmetric clamp arms 705, but only one is viewable in FIG. 7.

On the lower end of the clamp arm 705, there may be a rod 122' that serves a similar purpose as rod 122 in the attachment mechanism discussed above and shown in FIG. 3 (e.g., rod 122' may latch onto a channel 112 of the ultrasound imaging apparatus 110).

The clamp arm 705 may be attached to a biasing mechanism 715 (e.g., a spring) that biases the lower portion of the clamp arm 705 (and the rod 122') towards a closed (e.g., latched) position that would engage the channel 112 of the ultrasound imaging apparatus 110.

In the illustrated embodiment, the clamp arm 705 may be provided in a 'r' or '7' shape, where a hinge 710 is provided at the bend point. The upper portion of the clamp arm 705 may extend towards the vertical center line of the add-on vibration inducing device 120'. The biasing mechanism 715 may be mated to the upper portion of the clamp arm 705. In an example embodiment, the biasing mechanism 715 may be attached to the bracket 128 discussed above.

In some embodiments, rod 122' may be provided with a beveled edge so that it can more easily slide over a top surface of the ultrasound imaging apparatus 110. When sliding over the top surface of the ultrasound imaging apparatus, the clamp arm 705 may move away from a side of the imaging apparatus 110 before the biasing mechanism 715 engages to rotate the clamp arm 705 around the hinge 710 and position the clamp arm 705 into the latched position.

To release a clamp arm 705, force 750 can be applied to a button 730 on the top of the add-on vibration inducing device 120'. When pressed, the button 730 lowers the top portion of the clamp arm 705 adjacent the biasing mechanism 715. This in turn, would depress the biasing mechanism 715 and pivot the clamp arm 705 around the hinge 710 so as to move the lower portion of the clamp arm 705 (and thus rod 122') to the open position (e.g., an unlatched position where the rod 122' is moved away from the channel 112 of the ultrasound imaging apparatus 110). This may allow the add-on vibration inducing device 120' to be detached and removed from the ultrasound imaging apparatus 110.

The mechanism described in FIG. 7 sufficiently allows for the attachment and detachment of the add-on vibration inducing device 120' to the ultrasound imaging apparatus 110 for the purposes of generating shear waves as discussed herein. However, in some embodiments, the add-on vibration inducing device 120' may optionally be provided with a further lock feature that secures the connection between the add-on vibration inducing device 120' and the ultrasound imaging apparatus 110, and reduces the chance of the add-on vibration inducing device 120' being accidentally detached. This optional lock feature is discussed below with respect to FIG. 7, but it is not necessary in all embodiments.

In some embodiments, the button 730 may act as this lock feature by being configured to be rotatable to lock the clamp arms 705 in a closed position. For example, the button 730 may be attached to a turnpiece, which itself may further be attached to a plate 770 that rotates with the rotation of the button 730. FIG. 7 shows the lock feature being in an unlocked position where the button 730 can be freely depressed, and the upper portions of the clamp arm 705 mated to the biasing mechanism 715 can move freely.

Figure 8:
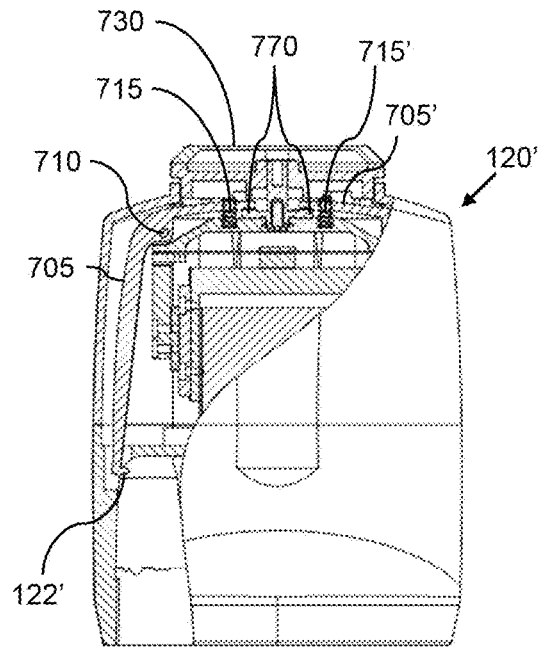

Referring to FIG. 8 shown there is a detailed view of the attachment system in the add-on vibration inducing device of FIG. 7 with its lock feature in a locked position, in accordance with at least one embodiment of the present invention. FIG. 8 shows when the button 730 is rotated to the lock position. In this position, the ends of the plate 770 are also rotated so as to be adjacent the biasing mechanisms 715, 715' and positioned under the upper portions of clamp arms 705, 705'. This prevents the button 730 and the biasing mechanisms 715, 715' from being depressed. As a result, the clamp arms 705, 705' are prevented from pivoting around the hinge 710, and the clamp arms 705, 705' are locked in a closed position. In some embodiments, small bumps may be provided on the top surface(s) of the plate 770 that mate with the bottom surface(s) of the upper portions of the clamp arms 705, 705'. These small bumps may facilitate ease of slidable engagement between the two surfaces.

Figure 9:
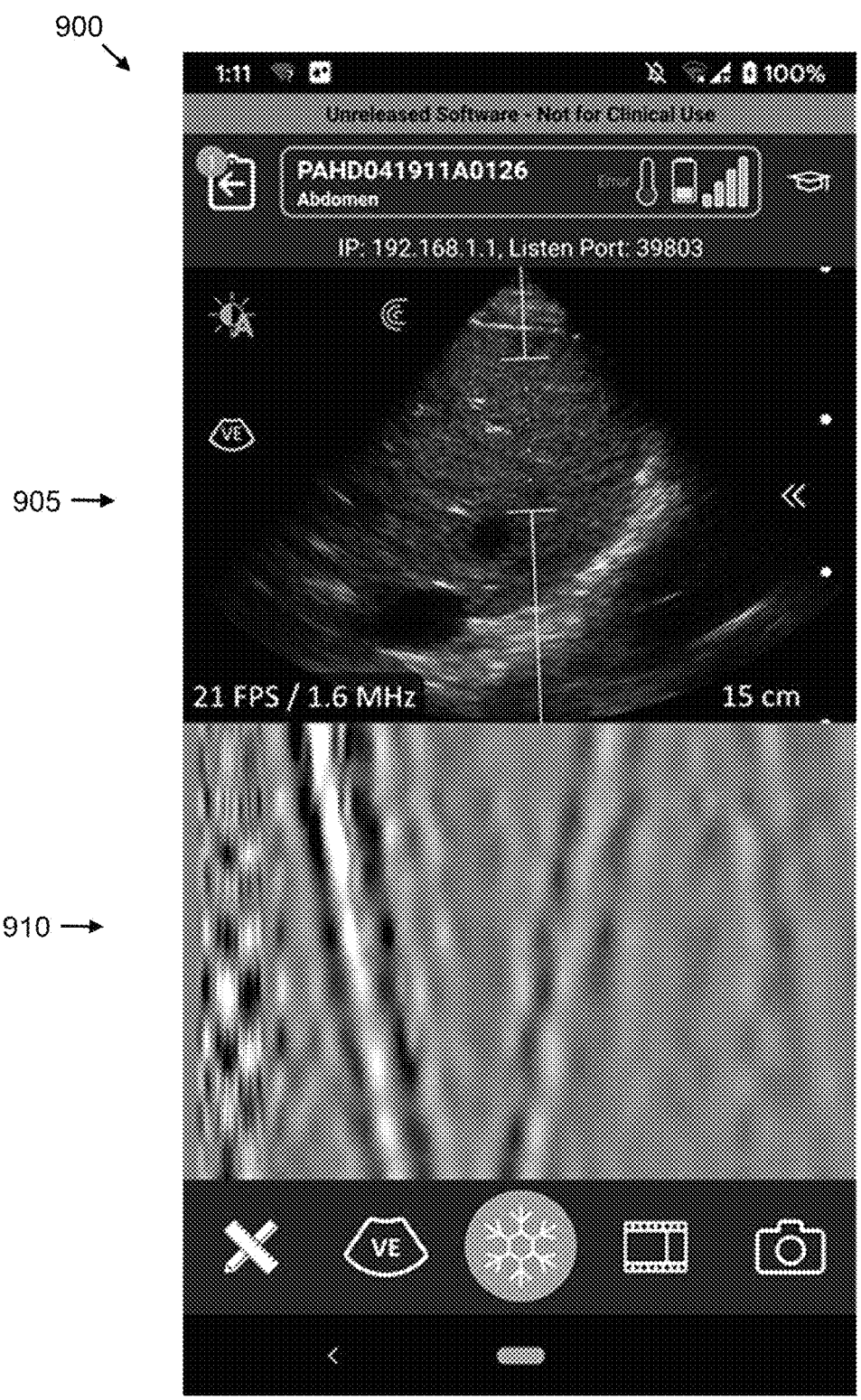
FIG. 9 shows an example user interface that may be displayed when an ultrasound imaging system with an add-on vibration inducing device is used to generate shear waves, in accordance with at least one embodiment of the present invention.

Referring to FIG. 9, shown there generally as 900 is an example user interface that may be displayed when an ultrasound imaging apparatus 110 with an add-on vibration inducing device 120, 120' is used to generate shear waves in tissue, in accordance with at least one embodiment of the present invention. In some embodiments, the user interface 900 may be shown on a user interface device 170 communicably coupled to the ultrasound imaging apparatus 110, as discussed above.

For example, the user interface 900 may have a portion that shows a typical ultrasound bright-mode (B-mode) image 905. In the illustrated embodiment, a gate may be shown in the B-mode image portion 905 that can be positioned by a user to provide an indication of the desired location of the volume of tissue to be explored.

The example user interface may also have another portion 910 which provides a graphical representation of the velocity of the shear wave generated by the add-on vibration inducing device 120, 120' in the tissue. The graphical representation shown in user interface portion 910 may generally reflect the time the shear wave takes to travel a particular depth inside the explored tissue. For example, in the graphical representation, the vertical axis may correspond to depth and the horizontal axis may correspond to time. While not particularly illustrated in the example of FIG. 9, various shear propagation parameters as discussed above may also be displayed in the user interface.

At least one advantage of the present invention compared to other imaging apparatus from the prior art which use shear waves is that ultrasound imaging apparatus 110 can be used independently from the add-on vibration inducing device 120 for performing ultrasound diagnostic procedures and the add-on vibration inducing device 120 can be easily mounted on the ultrasound imaging apparatus 110, and the entire assembly can be easily operated when an elastography diagnostic procedure needs to be performed.

While a number of exemplary aspects and embodiments have been discussed above, those of skill in the art will recognize that may be certain variations, modifications, permutations, additions and sub-combinations thereof. While the above description contains many details of example embodiments, these should not be construed as essential limitations on the scope of any embodiment. Many other ramifications and variations are possible within the teachings of the various embodiments.

We claim:

1. An ultrasound imaging system comprising:
   a probe operable to acquire ultrasound image data; and
   an add-on vibration inducing device operable to generate shear waves and powered without a corded connection, the add-on vibration inducing device being attachable to the probe and when attached, the add-on vibration inducing device cordlessly receives from the probe control signals that control generation of the shear waves for performing elastography diagnostic methods.

2. The ultrasound imaging system of claim 1 wherein the add-on vibration inducing device comprises a connector which cordlessly connects to a power connector on the probe for transmitting power from the probe to the add-on vibration inducing device.

3. The ultrasound imaging system of claim 2 wherein the probe has a battery which powers the add-on vibration inducing device through the connection between the power connector and the connector.

4. The ultrasound imaging system of claim 1 wherein a longitudinal axis of the add-on vibration inducing device coincides with a longitudinal axis of the probe.

5. The ultrasound imaging system of claim 1 wherein the add-on vibration inducing device is mounted on the probe through a lock feature provided on the probe which cooperates with a lock feature provided on the add-on vibration inducing device such that the shear waves signals generated by the add-on vibration inducing device are securely transmitted to the probe.

6. The ultrasound imaging system of claim 5 wherein the lock feature on the add-on vibration inducing device comprises a rod which can be positioned to fit within the lock feature provided on the probe which is in the shape of a channel.

7. The ultrasound imaging system of claim 1 wherein the add-on vibration inducing device comprises a voice coil actuator which-moves coaxially to generate shear waves signals.

8. The ultrasound imaging system of claim 1 wherein a bearing block is attached either directly or through an intermediary component to a housing of the vibration inducing device and a linear rail is attached to a housing of the voice coil actuator such that the bearing block and the linear rail cooperate to allow the co-axial motion of the voice coil actuator.

9. The ultrasound imaging system of claim 7 wherein the add-on vibration inducing device further comprises a first stage DC/DC converter for limiting the voltage transmitted from a battery of the probe to the vibration inducing device when the probe needs more power, a first capacitor which transmits the power from the first stage DC/DC converter to a second stage DC/DC converter which regulates the voltage transmitted through a second capacitor to a voice coil actuator driver which controls and monitors the voice coil actuator.

10. The ultrasound imaging system of claim 9 further comprising a microcontroller which controls the voice coil actuator driver to thereby control the vibration signals generated by the add-on vibration inducing device according to the commands transmitted by the probe.

11. The ultrasound imaging system of claim 1 wherein the probe is wired to a user interface device or is wirelessly connected to a user interface device which transmits control signals to the probe and to the add-on vibration inducing device.

12. The ultrasound imaging system of claim 1 wherein the add-on vibration inducing device is activated by a push button located on the probe or is activated by a user interface device communicably coupled to the probe.

13. The ultrasound imaging system of claim 1 wherein the connection between the probe and the add-on vibration inducing device is through a wireless, radio-wave based communication interface.

14. The ultrasound imaging system of claim 1 wherein the probe is configured to be used separately of the add-on vibration inducing device for ultrasound imaging diagnostics other than elastography methods.

15. A method for operating an ultrasound imaging system which comprises a probe connected to an add-on vibration inducing device to generate shear waves for performing an elastography diagnostic procedure, the method including:
    generating an activation signal through a push button on the probe or through a user interface device connected to the probe; and
    transmitting the activation signal cordlessly from the probe to the add-on vibration inducing device, the add-on vibration device being powered without a corded connection, the activation signal commanding the add-on vibration inducing device to generate shear waves, for performing an elastography diagnostic method.

16. The method of claim 15 wherein the add-on vibration inducing device comprises a connector which connects to and communicates with power connector located on the probe.

17. The method of claim 16 further comprising providing electrical power from a battery located within the probe to the add-on vibration inducing device through the power connector which communicates with the connector.

18. The method of claim 17 further comprising limiting the electrical power transmitted from the battery through a first DC/DC converter to a first capacitor of the add-on vibration device when the probe needs more power and providing stable regulated power from the first capacitor through a second stage DC/DC converter and through a second capacitor to a driver of a voice coil actuator within the add-on vibration device when the activation signal for generating shear wave signals is received from the probe.

19. The method of claim 18 further comprising controlling and monitoring the operation of the driver of the voice coil actuator by a microcontroller according to commands received by the microcontroller from the probe and providing feedback from the voice coil actuator to the microcontroller.

20. The method of claim 15 wherein the connection between the probe and the add-on vibration inducing device is through a wireless, radio-wave based, communication interface.

* * * * *